(12) United States Patent
Goto et al.

(10) Patent No.: US 7,709,032 B2
(45) Date of Patent: May 4, 2010

(54) ANTI-ALLERGIC AGENT CONTAINING BOTH GROUND LOTUS AND/OR EXTRACT AND LACTIC ACID BACTERIUM

(75) Inventors: Kiyoshi Goto, Saitama (JP); Haruhisa Wago, Sayama (JP)

(73) Assignee: Toyo R&D Inc., Sayama-Shi, Saitama (JP)

( * ) Notice: Subject to any disclaimer, the term of this patent is extended or adjusted under 35 U.S.C. 154(b) by 705 days.

(21) Appl. No.: 10/596,231

(22) PCT Filed: Dec. 5, 2003

(86) PCT No.: PCT/JP03/15611

§ 371 (c)(1),
(2), (4) Date: Mar. 9, 2007

(87) PCT Pub. No.: WO2005/053722

PCT Pub. Date: Jun. 16, 2005

(65) Prior Publication Data

US 2007/0269415 A1 Nov. 22, 2007

(51) Int. Cl.
C12N 1/20 (2006.01)
A61K 36/18 (2006.01)
A61K 48/00 (2006.01)

(52) U.S. Cl. .................. 424/773; 424/725; 424/93.4

(58) Field of Classification Search ........... 424/725, 424/773, 93.4; 435/252.1
See application file for complete search history.

(56) References Cited

U.S. PATENT DOCUMENTS 6,685,973 B1 * 2/2004 Kung-Ming ............ 424/757

FOREIGN PATENT DOCUMENTS

| EP | 1 260 227 A1 | 11/2002 |
|---|---|---|
| JP | 61291524 | 12/1986 |
| JP | 63-14680 A | 1/1988 |
| JP | 1121217 | 5/1989 |
| JP | 7215884 | 8/1995 |
| JP | 9002959 | 1/1997 |
| JP | 11199495 | 7/1999 |
| JP | 2000-297044 A | 10/2000 |
| JP | 2003-238437 A | 8/2003 |
| WO | WO 02/080946 | * 10/2002 |
| WO | WO 2004/067019 A1 | 8/2004 |

OTHER PUBLICATIONS

Li Qingchun et al. Fermentation of Lotus Roots with Lactic Acid Bacteria, Shipin Kexue (Beijing), 2000, vol. 21, No. 10, pp. 41-43: Chemical Abstracts. Abs. No. 134:221718.
Kim, D. et al. Combination of Natural Products Removing ROS . . . Korean J. Microbiology and Biotechnology, 2002, 30 (3), pp. 270-281 (abstract), EMBASE[online]; AN. 2003463598.
Haruhisa Wago et al. Effects of Anti-Allergic Vegetable and Teas on IL-4 Production of . . . Bulletin of Saitama Medical School Junior College Kiyo, 1999, vol. 10, pp. 11-15.
Haruhisa Wago et al. Effects of Vegetable Soups on IgG and IgE in the Blood of Mice Which . . . Bulletin of Saitama Medical School Junior College Kiyo, 1999, vol. 10, pp. 1-5.
Naohisa Wago et al. Renkon Nettsusui Chushutsubutsu Ko-Allergy Sayo-IgE . . . Japanese Society for Immunology Sokai Gakujutsu Shukai Kiroku, Nov. 5, 2003 vol. 33, p. 163.
Yukio Tanaka et al. Rat no Ko Enkikyu Hakketsubyo . . . edited by Proceedings of Osaka Prefectural Institute of Public Health.Ed. of food Sanitation, 1991, vol. 22, pp. 7-13.
Hiroshi Kano et al. Oral administration of milk fermented with *Lactobacillus delbrueckii* ssp., bulgaricus OLL1073R-1 to . . . Cyto technology, 2002. vol. 40, No. 1/3, pp. 67-73.
T. Matsuzaki et al. The Effect of Oral Feeding of *Lactobacillus casei* Strain Shirota on Immunoglobulin E Production in Mice J. Dairy Science, 1998, vol. 81, No. 1, pp. 48-53.
Y. Nomura et al. Oral Administration of Lactosucrose Suppresses Endogenous Production of TNF . . . Biotherapy, 1997, vol. 11, No. 3, pp. 438-441.

* cited by examiner

*Primary Examiner*—Ruth A Davis
(74) *Attorney, Agent, or Firm*—Cozen O'Connor

(57) ABSTRACT

The present invention relates to an anti-allergic agent, an anti-allergic food additive and an anti-allergic food each containing both ground lotus and/or extract and a lactic acid bacterium. The anti-allergic agent, anti-allergic food additive and anti-allergic food each contain both ground lotus and/or extract and a lactic acid bacterium as the active ingredients thereby enabling amelioration and treatment of allergic diseases including pollinosis, bronchial asthma and atopic dermatitis.

6 Claims, No Drawings

ANTI-ALLERGIC AGENT CONTAINING BOTH GROUND LOTUS AND/OR EXTRACT AND LACTIC ACID BACTERIUM

TECHNICAL FIELD

The present invention relates to an anti-allergic agent, an anti-allergic food additive and an anti-allergic food each of which contains ground lotus (*Nelumbo nucifera*) and/or a lotus extract and a lactic acid bacterium.

BACKGROUND ART

In many developed nations, diseases attributable to type I allergic reactions such as pollinosis (hay fever), bronchial asthma or atopic dermatitis are on the increase and becoming a social problem.

Among 5 kinds of antibodies possessed by humans, an antibody called IgE is involved particularly in type I allergic reaction, and this antibody tends to be produced in a larger amount in persons with an allergic constitution than in healthy persons without an allergic constitution. Production of IgE is promoted by interleukin 4 (IL-4) or interleukin 13 (IL-13) derived form type 2 helper T lymphocyte (Th2), and is reported in recent years to be inhibited by interleukin 2 (IL-2) or interferon γ (IFN-γ) derived from type I helper T lymphocyte (Th1). For ameliorating the allergic constitution, therefore, it is important to inhibit production of IgE by inhibiting the production of IL-4 or IL-13 or by promoting the production of IL-2 or IFN-γ. In addition, TNF (tumor necrosis factor) is also involved in type I allergic reaction and thus inhibition of TNF production is also effective in inhibiting inflammatory reactions.

For ameliorating diseases by the above type I allergic reaction, pharmaceutical preparations such as antihistamines, anti-allergic agents and steroids have been developed and used so far. These chemicals may be accompanied by side effects such as worsening of morbid state due to long-term administration (rebound phenomenon), sleepiness by their action on the central nerves, their influence on the internal secretory system by transdermal absorption, etc.

For the purpose of ameliorating the diseases safely without side effects, on the other hand, foods having an anti-allergic action have been searched for from conventionally eaten foods (see JP-A No. 61-291524, JP-A No. 1-121217, JP-A No. 7-215884 etc.). Further, previously marketed and widely recognized drinks include a sweet tea extract made from leaves of *Rubus Suavissimus* with hot water and a beefsteak plant extract made from a beef steak plant (*Perilla frutescens*) with hot water. Also, lactic acid bacteria have an action of inducing Th1 cells from the viewpoint of probiotics and are thus examined as anti-allergic material.

However, a majority of compounds used as pharmaceutical preparations are problematic because of the side effects mentioned above. There are also food-derived anti-allergic materials such as a sweet tea extract and a beefsteak plant leaf extract, but from the viewpoint of different working mechanisms, greater efficacy and/or economical advantage, there is a need for utilizing anti-allergic materials derived from other foods. The anti-allergic action of lactic acid bacteria is problematic due to the low action of lactic acid bacteria when used on its own.

DISCLOSURE OF INVENTION

The present inventors found that a composition comprising ground lotus and/or a lotus extract and lactic acid bacteria has an anti-allergic action, and on the basis of this finding, the present invention was completed.

The present invention provides an anti-allergic agent, an anti-allergic food additive and an anti-allergic food each comprising ground lotus and/or a lotus extract and a lactic acid bacterium.

The present invention also provides a pollinosis-relieving agent, a pollinosis-relieving food additive, and a pollinosis-relieving food, each comprising ground lotus and/or a lotus extract and a lactic acid bacterium.

The present invention also provides an agent for lowering IgE levels in serum, a food additive for lowering IgE levels in serum, and a food for lowering IgE levels in serum, each comprising ground lotus and/or a lotus extract and a lactic acid bacterium.

The present invention also provides an agent for inhibiting the production of IL-4, a food additive for inhibiting the production of IL-4, and a food for inhibiting the production of IL-4, each comprising ground lotus and/or a lotus extract and a lactic acid bacterium.

The present invention also provides an agent for inhibiting the production of TNF, a food additive for inhibiting the production of TNF, and a food for inhibiting the production of TNF, each comprising ground lotus and/or a lotus extract and a lactic acid bacterium.

In the present invention, the "lotus" refers to *Nelumbo nucifera* belonging to the subfamily Nelumboideae in the family Nymphaeaceae. A subterranean stem of the lotus is generally called "lotus root" and commercially available.

When preparing the lotus to be formed into ground lotus or extract of the present invention, any part of the lotus plant can be used, and examples thereof include, but are not limited to, a subterranean stem (lotus root), stem, leaf, root or seed of the lotus, and a combination thereof. The lotus used in a ground state or as an extract is preferably a subterranean stem, stem, leaf or root of the lotus, or a combination thereof, more preferably a subterranean stem, stem or leaf of the lotus, or a combination thereof, still more preferably a subterranean stem of the lotus.

The ground lotus can be prepared by grinding a lotus by any method using a simple mixer or a mill. This grinding may be carried out in an embodiment where a lotus in the presence of a solvent such as water, or a lotus only, is ground. The ground lotus in the present invention may be a ground lotus untreated or may have been subjected to heating and/or dehydration before, during or after milling. Heating and/or dehydration may or may not be carried out.

Preferable examples of the ground lotus include, but are not limited to, a product obtained by grinding a lotus, then heating and drying it, a product obtained by drying a lotus and grinding it, a product obtained by heating a lotus and grinding it, and a product obtained by heating and drying a lotus (the order of heating and drying is not restricted) and then grinding it. In a certain embodiment, an intact lotus may be subjected directly to a drying treatment such as freeze-drying or drying with infrared light and then ground.

The ground lotus may be a concentrate of the lotus from which water is partially removed, and in this case, the concentrating treatment in preparation of the ground lotus includes, but is not limited to, an embodiment in accordance with the drying treatment described above.

The ground product can be in any form such as paste, solid, granules, powder, liquid (including any state such as a solution and suspension), and the ground product in such form can be produced by any method known in the art. For example, the ground product can be prepared so as to be in such form directly from a lotus; or as described above, the ground product obtained once in a dry state by drying treatment can be prepared so as to be in such form.

When the drying or concentrating treatment is carried out in preparation of the ground lotus, the method of drying or concentrating treatment may be any method known in the art, which includes, but is not limited to, a freeze-drying method (method of drying under reduced pressure), a concentrating method under reduced pressure, a method of drying with microwaves under reduced pressure, a method of drying with microwaves at normal pressures and a heating drying method such as drying with far infrared light or drying with near infrared light. Preferably, the method of drying or concentrating treatment is a freeze-drying method, a concentrating method under reduced pressure or a method of drying with far infrared light.

When the drying or concentrating treatment is carried out in preparation of the ground lotus, the treatment temperature varies depending on the method used, but is preferably −50° C. to 100° C., more preferably −30° C. to 70° C., still more preferably −30° C. to 60° C.

Besides heating conducted sometimes in the drying or concentrating treatment in preparation of the ground lotus, heating treatment for unlimited purposes such as sterilization may be conducted. In this case, the heating temperature is preferably 100° C. or less. That is, it is preferable that a temperature of higher than 100° C. is not applied in the process of forming the lotus into the ground lotus.

As one preferable embodiment of the ground lotus used in the present invention, mention is made of a freeze-dried or far infrared light-dried ground lotus prepared by a method including either a step 1) wherein a lotus is ground, and the resulting ground lotus is freeze-dried or dried with far infrared light or a step 2) wherein a lotus is freeze-dried or dried with far infrared light, and then the dried lotus is ground.

In the present invention, the lotus extract is not limited to an extract obtained by extraction treatment with a solvent to transfer components in the lotus into the solvent, and extracts (e.g., a fluid obtained by pressing a lotus) prepared by extracting any component from a lotus directly without a solvent or the like also fall under the scope of the extract referred to in the present invention. The extract may be prepared at room temperature, or may be prepared under heating. Examples of the lotus extract include, for example, juices obtained by pressing thinly cut or ground lotuses, juices obtained by pressing thinly cut or ground lotuses under heating, and extracts obtained by extracting thinly cut or ground lotuses with a solvent with or without heating. The solvent usable in solvent extraction includes water, ethanol, propylene glycol, n-butanol, ethyl acetate, chloroform, and a mixed solvent of two more substances thereof. The solvent used in extraction is preferably water. The extract can be concentrated or evaporated to dryness if necessary. The extract can be in any form such as paste, solid, granules, powder, liquid (including an extract in any state such as solution and suspension), and the extract in such form can be produced in any known method.

When the drying or concentrating treatment is carried out in preparation of the lotus extract, the method of drying or concentrating treatment may be any method known in the art, which includes, but is not limited to, a freeze-drying method (method of drying under reduced pressure), a concentrating method under reduced pressure, a method of drying with microwaves under reduced pressure, a method of drying with microwaves at normal pressures and a heating drying method such as drying with far infrared light or drying with near infrared light. Preferably, the method of drying or concentrating treatment is a freeze-drying method, a concentrating method under reduced pressure or a method of drying with far infrared light.

When the drying or concentrating treatment is carried out in preparation of the lotus extract, the treatment temperature varies depending on the method used, but is preferably −50° C. to 100° C., more preferably −30° C. to 70° C., still more preferably −30° C. to 60° C.

Besides heating conducted sometimes in the drying or concentrating treatment in preparation of the lotus extract, heating treatment for unlimited purposes such as sterilization may be conducted. In this case, the heating temperature is preferably 100° C. or less. That is, it is preferable that a temperature of higher than 100° C. is not applied in the process of forming the lotus into the lotus extract.

As one preferable embodiment of the lotus extract used in the present invention, mention is made of a freeze-dried or far infrared light-dried lotus extract prepared by a method including a step wherein a lotus root is subjected to extraction, and the resulting lotus extract is freeze-dried or dried with far infrared light. In another embodiment, a lotus extract concentrated under reduced pressure, prepared by a method including a step of concentrating the lotus extract under reduced pressure, can be mentioned.

In the present invention, the ground lotus and/or the lotus extract may be contained in a composition, a drug, a food additive and a food.

The lactic acid bacteria used in the present invention include, but are not limited to, lactic acid bacteria belonging to the genera *Lactobacillus, Streptococcus, Bifidobacterium* and *Bacillus*. From the viewpoint of allowing orally ingested lactic acid bacteria to be alive and easily arrive at the intestine, the lactic acid bacteria are preferably sporing lactic acid bacteria. For example, the sporing lactic acid bacteria include, but are not limited to, *Bacillus coagulans* etc.

A first embodiment of the invention is an anti-allergic agent comprising ground lotus and/or a lotus extract and a lactic acid bacterium, wherein the anti-allergic agent is a drug for ameliorating and treating diseases attributable to allergic reaction, preferably a drug for ameliorating and treating diseases attributable to type I allergic reaction. The anti-allergic agent of the present invention is more preferably a drug for ameliorating or treating pollinosis (in the present invention, pollinosis refers to symptoms attributable to allergic reaction to pollen, and the major symptom includes, but is not limited to, nasal mucus, nasal congestion, sneezing, itching of the eyes, sore throat etc.), dermatitis including atopic dermatitis, or bronchial asthma, or a combination thereof, that is, a pollinosis-relieving agent, a dermatitis-relieving agent, an atopic dermatitis-relieving agent or a bronchial asthma-relieving agent. The anti-allergic agent of the present invention is more preferably a pollinosis-relieving agent. In another preferable embodiment, the anti-allergic agent of the present invention is an agent for reducing IgE levels in serum, which is used in reducing IgE levels in serum. In another preferable embodiment, the anti-allergic agent of the present invention is an agent for inhibiting the production of IL-4. In another preferable embodiment, the anti-allergic agent of the present invention is an agent for inhibiting the production of TNF-α.

The anti-allergic agent of the present invention can be administered orally or parenterally through intramuscular, intradermal, subcutaneous, intravenous, lower body cavity, skin or nasal cavity administration, or oral or nasal inhalation. The drug of the present invention can contain constituent ingredients allowable as drug, and the constituent ingredients are an item recognized by those skilled in the art and are not particularly limited. For manufacturing a pharmaceutical preparation of the anti-allergic agent of the present invention, the drug can be formed into a pharmaceutical preparation by any usual method in the technical field of pharmaceutical manufacturing, and for example, pharmaceutical forms such as tablets, granules, powder, capsules, syrups and troches can be used for oral administration. In the case of transdermal administration, mention is made of an ointment, a poultice, a lotion and an aerosol. That is, when a solid pharmaceutical preparation for oral administration is prepared, an excipient and if necessary a binder, a lubricant, a coloring agent, a taste corrective and a flavor corrective can be added to the ground lotus and/or the lotus extract and formed in a usual manner into tablets, granules, powder, capsules, troches, sugar-coated tablets, etc.

With respect to the dose of the drug of the invention administered orally to humans, the amount of the ground lotus on a dry-weight basis is preferably 1 to 100 g, more preferably 2 to 40 g, per day for adult. The amount of the lotus extract on a dry-weight basis is preferably 0.5 to 50 g, more preferably 1 to 20 g, per day for adult. The daily dose of lactic acid bacteria orally administered to human adults is preferably 500,000 to 5 billion (bacteria), more preferably 5 million to 1 billion (bacteria), in terms of the number of bacteria.

Another embodiment of the present invention is an anti-allergic food additive comprising ground lotus and/or a lotus extract and a lactic acid bacterium. The food additive in the present invention may be an additive which can be added to a food, and the object thereof is not limited. The anti-allergic food additive is a food additive for ameliorating and treating diseases attributable to allergic reactions for persons who have ingested food containing the food additive, preferably a food additive for ameliorating and treating diseases attributable to type I allergic reaction. The anti-allergic food additive of the present invention is more preferably a food additive for ameliorating or treating pollinosis, dermatitis including atopic dermatitis, or bronchial asthma, or a combination thereof, that is, a pollinosis-relieving food additive, a dermatitis-relieving food additive, an atopic dermatitis-relieving food additive or a bronchial asthma-relieving food additive. The anti-allergic food additive of the present invention is more preferably a pollinosis-relieving food additive. In another preferable embodiment, the anti-allergic food additive of the present invention is a food additive for reducing IgE levels in serum. In another preferable embodiment, the anti-allergic food additive of the present invention is a food additive for inhibiting the production of IL-4. In another preferable embodiment, the anti-allergic food additive of the present invention is a food additive for inhibiting the production of TNF.

The food additive in the present invention may be an additive which can be added to a food, and the object thereof is not limited. For production of the food additive of the present invention, the food additive can be produced in the form of solid, granules, powder, capsules, solution, suspension etc. by a usual method in the technical field of food additive. The food additive of the present invention can contain another ingredient acceptable as food additive, and the other ingredient is an item recognized by those skilled in the art, and is not particularly limited.

The amount of the ground lotus and/or the lotus extract contained in the food additive of the present invention, the amount of lactic acid bacteria contained therein, and the proportion of these ingredients contained therein are not particularly limited and vary depending on the amount of the food additive added to food and the type of the food.

Another embodiment of the present invention is an anti-allergic food comprising ground lotus and/or a lotus extract and a lactic acid bacterium, wherein the anti-allergic food is a food for ameliorating and treating diseases attributable to allergic reaction, preferably a food for ameliorating and treating diseases attributable to type I allergic reaction. The anti-allergic food of the present invention is more preferably a food for ameliorating or treating pollinosis, dermatitis including atopic dermatitis, or bronchial asthma, or a combination thereof, that is, a pollinosis-relieving food, a dermatitis-relieving food, an atopic dermatitis-relieving food or a bronchial asthma-relieving food. The anti-allergic food of the present invention is more preferably a pollinosis-relieving food. In another preferable embodiment, the anti-allergic food of the present invention is a food for reducing IgE levels in serum. In another preferable embodiment, the anti-allergic food of the present invention is a food for inhibiting the production of IL-4. In another preferable embodiment, the anti-allergic food of the present invention is a food for inhibiting the production of TNF.

The food in the present invention is not particularly limited as far as it contains the ground lotus and/or the lotus extract and lactic acid bacteria. The type of food is not particularly limited as far as it is to be ingested usually as food, and the food includes, but is not limited to, foods called health food or food supplements informs such as tablets, granules, powder and capsules, noodles including udon (thick white noodles), buckwheat noodles, pasta and ramen, flour such as wheat flour, buckwheat flour, starch, and rice flour, bread such as sweet roll and sliced bread, confectionery such as cake, cookie, rice cracker, bean jam, yokan (sweetened and jellied bean paste), rice cake, dumpling and jelly, drinks such as juice and tea, and instant foods such as instant Chinese noodles, instant miso soup, and instant soup. The foods of the present invention are preferably foods such as bread, cake, cookie and rice cracker produced from flour such as wheat flour, buckwheat flour, starch, and rice flour containing the ground lotus and/or the lotus extract and lactic acid bacteria. The foods of the present invention are more preferably foods such as bread, cake, cookie and rice cracker produced from flour such as wheat flour, buckwheat flour, starch, and rice flour containing the ground lotus and/or the lotus extract in a powdery form and lactic acid bacteria. In another preferable embodiment, the food of the present invention is yogurt containing the ground lotus and/or the lotus extract and lactic acid bacteria. As used herein, yogurt includes not only usual semi-solid yogurt but also liquid yogurt such as a yogurt drink. In production of the food of the present invention, any known methods and materials can be used.

The amounts of the ground lotus and/or the lotus extract and lactic acid bacteria contained in the food of the present invention, and the proportion of these ingredients contained therein, are not particularly limited as far as the food of the present invention can demonstrate its effect.

The food of the present invention is in such a food form as to allow the ground lotus in an amount of preferably 1 to 100 g, more preferably 2 to 40 g, on a dry-weight basis, to be ingested per day by a human adult, or in such a food form as to allow the lotus extract in an amount of preferably 0.5 to 50 g, more preferably 1 to 20 g, on a dry-weight basis, to be ingested per day by a human adult. The food of the present invention is also in such a food form that in oral administration, lactic acid bacteria in an amount of preferably 500,000 to 5 billion, more preferably 5 million to 1 billion, in terms of the number of bacteria, are ingested per day by a human adult.

The food of the present invention can be produced by adding the ground lotus and/or the lotus extract, and lactic acid bacteria, to a starting material constituting the food, or by adding the food additive of the present invention to a starting material constituting the food. Depending on the type of food, the food additive of the present invention can be added to a produced food thereby constituting the food of the present invention.

Although not wished to be bound by theory, it is believed that one mechanism of anti-allergic action upon oral administration of the ground lotus and/or the lotus extract into mammals including humans results from the in vivo inhibition, by oral administration of the anti-allergic agent, of production of interleukin 4 (1-L-4) derived from type 2 helper T lymphocyte (Th2) and the subsequent inhibition of production of IgE in B cells. It is also believed that another mechanism results from the inhibition of inflammation reaction by the in vivo inhibition of production of TNF, preferably TNF-α, by oral administration of the anti-allergic agent. The possibility of these working mechanisms is described in detail in PCT/03/09208. The above examples are mentioned as the working mechanism of the ground lotus and/or the lotus extract, but do not exclude other working mechanisms.

Although not wished to be bound by theory, it is believed that the mechanism of the anti-allergic action upon oral administration of lactic acid bacteria into mammals including humans, though not completely revealed, is attributable to the effect of inducing Th1 cells, from the probiotics of lactic acid bacteria.

The anti-allergic agent, anti-allergic food additive and anti-allergic food of the present invention each comprise ground lotus and/or a lotus extract and a lactic acid bacterium as active ingredients thereby exhibiting an advantageous effect of enabling significantly synergistic amelioration or treatment of allergic diseases including pollinosis, bronchial asthma and dermatitis such as atopic dermatitis, as compared with the case where ground lotus and/or a lotus extract, or a lactic acid bacterium, is used alone.

Each of the drug, food additive and food of the present invention comprises ground lotus and/or a lotus extract and a lactic acid bacterium as active ingredients thereby exhibiting an advantageous effect of enabling significantly synergistic reduction in IgE levels in serum, as compared with the case where ground lotus and/or a lotus extract, or a lactic acid bacterium, is used alone.

Each of the drug, food additive and food of the present invention comprises ground lotus and/or a lotus extract and a lactic acid bacterium as active ingredients thereby exhibiting an advantageous effect of enabling significantly synergistic inhibition of production of IL-4 in the living body, as compared with the case where ground lotus and/or a lotus extract, or a lactic acid bacterium, is used alone.

Each of the drug, food additive and food of the present invention comprises ground lotus and/or a lotus extract and a lactic acid bacterium as active ingredients thereby exhibiting an advantageous effect of enabling significantly synergistic inhibition of production of TNF in the living body, as compared with the case where ground lotus and/or a lotus extract, or a lactic acid bacterium, is used alone.

BEST MODE FOR CARRYING OUT THE INVENTION

Hereinafter, the present invention is described in more detail by reference to the Examples, but the present invention is not limited to the scope of the Examples.

EXAMPLES

In Examples 1 and 2 and Comparative Examples 1 to 4, the influence of successive ingestion of each drug on amelioration of human predisposition to pollinosis was examined.

In Examples 1 and 2 and Comparative Examples 1 to 4 below, subjects (males or females in the twenties to fifties) having a predisposition to pollinosis were 21 subjects in each group (9 males and 12 females).

The subjects ingested the anti-allergic agent by swallowing 10 tablets in water or hot water once per day for about 3 months (from early December to early March). During the test, the administration of another drug for amelioration of a predisposition to pollinosis was not carried out.

The degree of improvement of symptoms of pollinosis with respect to symptoms during the test (sneezing, nasal mucus, nasal congestion, itching of the eyes, watery eyes, a feeling of a foreign substance in the eye, feeling of physical disorder in the eyelid, flush on cheeks, headache, skin itching, pharyngeal itching, mouth itching, abnormal respiratory sound etc.) was self-assessed and reported by the subjects in 4 ranks (no improvement; light improvement; moderate improvement; significant improvement) relative to symptoms in the previous year before the test.

Example 1

Drug Containing a Lotus Root Extract and Lactic Acid Bacteria

1) Method of Preparing a Lotus Root Extract

One hundred kg commercial lotus root was peeled, then washed with water and cut into slices of 5 to 10 mm in thickness. Two hundred and sixty L water was added thereto, and the water and lotus root were introduced into a kneader and heated to 98° C. while stirring. After heating to 99° C., the sample was boiled for 30 minutes. Then, the boiled product was removed from the kneader and then filtered through bleached cotton to give a filtrate which was then powdered by freeze-drying. By this operation, 3.0 kg lotus extract powder was obtained.

2) Method of Preparing an Anti-Allergic Agent

The lotus extract (powder): sporing lactic acid bacteria for food (containing at least 5 billion bacteria) of *Bacillus coagulans* per g, and containing lactose as an excipient):maltose starch syrup were mixed at a ratio of 70:1:29, and the mixture was formed into spherical tablets (about 320 mg/tablet) of 8 mm in diameter, and this tablet was used as an anti-allergic agent.

3) Degree of Improvement of Symptoms of Pollinosis by Administration of the Anti-Allergic Agent As a result of ingestion of the anti-allergic agent for 3 months, it was recognized that among the 21 subjects, significant improvement was recognized in 12 subjects (9 females and 3 males), moderate improvement was recognized in 6 subjects (3 females and 3 males), and light improvement was recognized in 3 subjects (3 males). That is, light or more improvement was recognized in 100% of the subjects having a predisposition to pollinosis, as a result of the ingestion of the anti-allergic agent of the invention containing a lotus root extract and lactic acid bacteria.

Example 2

Drug Containing Ground Lotus Root and Lactic Acid Bacteria

1) Method of Preparing Ground Lotus Root

Commercial lotus root was peeled, then washed with water and cut into slices of 5 to 10 mm in thickness. The slices were heated at 110° C. for 15 minutes with a retort machine. After heating, the lotus root was cut thin, and the thinly cut lotus root was dried with hot water at 50 to 60° C. for 15 hours. Then, the sample was pulverized with an atomizer using a 1-mm screen to give ground lotus (powder).

2) Method of Preparing an Anti-Allergic Agent

The ground lotus root (powder): sporing lactic acid bacteria powder for food: maltose starch syrup were mixed at a ratio of 70:1:29, and the mixture was formed into spherical tablets (about 320 mg/tablet) of 8 mm in diameter, and this tablet was used as an anti-allergic agent.

3) Degree of Improvement of Symptoms of Pollinosis by Administration of the Anti-Allergic Agent As a result of ingestion of the anti-allergic agent for 3 months, it was recognized that among the 21 subjects, significant improvement was recognized in 9 subjects (6 females and 3 males), moderate improvement was recognized in 6 subjects (2 females and 4 males), and light improvement was recognized in 6 subjects (4 females and 2 males). That is, moderate or more improvement was recognized in 100% of the subjects with a predisposition to pollinosis, as a result of the ingestion of the anti-allergic agent containing ground lotus root and lactic acid bacteria.

Comparative Example 1

Drug Containing Only the Lotus Root Extract

Tablets were prepared in the same manner as in Example 1 except that the composition of the anti-allergic agent contained the lotus root extract prepared in Example 1 but did not contain the lactic acid bacteria.

That is, in Comparative Example 1, the lotus root extract prepared in Example 1: maltose starch syrup were mixed at a ratio of 70:30, and the mixture was formed into spherical tablets (about 320 mg/tablet) of 8 mm in diameter, and this tablet was used as an anti-allergic agent.

As a result of ingesting the anti-allergic agent for 3 months, it was recognized that among the 21 subjects, significant improvement was recognized in 3 subjects (2 females and 1 male), moderate improvement was recognized in 3 subjects (3 females), light improvement was recognized in 6 subjects (2 females and 4 males), and no improvement was recognized in the remaining 9 subjects (5 females and 4 males). That is, light or more improvement was recognized in 57% of the subjects with a predisposition to pollinosis, as a result of the ingestion of the anti-allergic agent containing only a lotus root extract.

Comparative Example 2

Ingestion of a Doubled Amount of the Drug Containing Only a Lotus Root Extract

The anti-allergic agent containing the lotus root extract but not containing the lactic acid bacteria, prepared in Comparative Example 1, was used, and the amount of the anti-allergic agent ingested by a subject was twice the quantity (20 tablets given once per day) of that in Comparative Example 1.

As a result of ingestion of the anti-allergic agent for 3 months, it was recognized that among the 21 subjects, significant improvement was recognized in 6 subjects (4 females and 2 males), moderate improvement was recognized in 3 subjects (1 female and 2 males), light improvement was recognized in 6 subjects (2 females and 4 males), and no improvement was recognized in the remaining 6 subjects (5 females and 1 male). That is, light or more improvement was recognized in 71% of the subjects with a predisposition to pollinosis, as a result of the ingestion of the anti-allergic agent containing a double amount of only a lotus root extract.

Comparative Example 3

Drug Containing Only Lactic Acid Bacteria

Tablets were prepared in the same manner as in Example 1 except that in Example 3 the composition of the anti-allergic agent contained the lactic acid bacteria but did not contain the lotus root extract.

That is, in Comparative Example 3, sporing lactic acid bacteria powder for food: maltose starch syrup were mixed at a ratio of 1:99, and the mixture was formed into spherical tablets (about 320 mg/tablet) of 8 mm in diameter, and this tablet was used as an anti-allergic agent.

As a result of ingestion of the anti-allergic agent for 3 months, it was recognized that among the 21 subjects, significant improvement was not recognized, moderate improvement was recognized in 3 subjects (2 females and 1 male) and light improvement was recognized in 3 subjects (1 female and 2 males). No improvement was recognized in the remaining 15 subjects (9 females and 6 males). That is, light or more improvement was recognized in 29% of the subjects with a predisposition to pollinosis as a result of the ingestion of the drug containing only the lotus root extract.

Comparative Example 4

Ingestion of a Doubled Amount of the Drug Containing Only the Lactic Acid Bacteria The anti-allergic agent containing the lactic acid bacteria but not containing the lotus root extract, prepared in Comparative Example 3, was used, and the amount of the anti-allergic agent ingested by a subject was twice the amount (20 tablets given once per day) of that in Comparative Example 3.

As a result of ingestion of the anti-allergic agent for 3 months, it was recognized that among the 21 subjects, significant improvement was recognized in 3 subjects (1 female and 2 males), moderate improvement was recognized in 3 subjects (3 females), light improvement was recognized in 3 subjects (2 females and 1 male), and no improvement was recognized in the remaining 12 subjects (6 females and 6 males). That is, light or more improvement was recognized in 43% of the subjects with a predisposition to pollinosis as a result of the ingestion of a double amount of the drug containing only the lotus root extract.

The results of the degrees of improvement of symptoms of pollinosis in Examples 1 and 2 and Comparative Examples 1 to 4 described above are shown in Table 1 below. The "improvement percentage (%)" in Table 1 is the ratio (percentage) of the number of subjects for whom light or more improvement was recognized, to the total number of subjects in each group.

TABLE 1

| Group | Presence or absence of: Lotus root | Presence or absence of: Lactic acid bacterium | degree of improvement (number of subjects) significant improvement | degree of improvement (number of subjects) moderate improvement | degree of improvement (number of subjects) light improvement | degree of improvement (number of subjects) no improvement | improvement percentage (%) |
|---|---|---|---|---|---|---|---|
| Example 1 | Extract | present | 12 | 6 | 3 | 0 | 100 |
| Example 2 | ground product | present | 9 | 6 | 6 | 0 | 100 |
| Comparative Example 1 | Extract | absent | 3 | 3 | 6 | 9 | 57 |
| Comparative Example 2 | Extract (2 fold) | absent | 6 | 3 | 6 | 6 | 71 |
| Comparative Example 3 | absent | present | 0 | 3 | 3 | 15 | 29 |
| Comparative Example 4 | absent | present (2 fold) | 3 | 3 | 3 | 12 | 43 |

As is evident from the results in Table 1, the anti-allergic agents of the present invention containing ground lotus and/or a lotus extract and lactic acid bacteria (Examples 1 and 2) not only exhibited an excellent pollinosis-ameliorating effect as compared with the case where each ingredient was used alone (Comparative Examples 1 and 3), but also exhibited a significantly excellent pollinosis-ameliorating effect as compared with the case where a double amount of each ingredient was used (Comparative Examples 2 and 4). This result revealed that the anti-allergic agent of the present invention exhibits a synergistic effect over the mere additive effect attained by using either the lotus root extract and/or ground lotus or lactic acid bacteria alone.

Example 3

Influence of the Successive Ingestion of the Anti-Allergic Agent of the Present Invention on Human Immune System In the subjects in Examples 1 and 2 and Comparative Examples 1 to 4, serum and lymphocytes were collected in the following method before and after the successive ingestion for 3 months, and used in the following experiment. All procedures were carried out aseptically, and any instruments used were previously sterilized.

1) Collection of Serum and Lymphocytes a) Ten ml venous blood was collected, 2 ml of the blood was introduced into a blood collection tube for serum separation, and the remainder was introduced into anticoagulant (sodium citrate)-containing 2 blood collection tubes in a volume of 4 ml per tube.

b) The blood collection tube for serum separation was left at 37° C. for 1 hour and centrifuged at 3000 rpm for 15 minutes, and the resulting serum was introduced into a microtube and stored in a frozen state at −80° C. until use.

c) To obtain lymphocytes from the peripheral blood, the blood collected in the anticoagulant-containing blood collection tube was diluted 2-fold with PBS (pH 7.2). This sample was layered on a human lymphocyte separation medium (LSM) with a specific gravity of 1.077 and centrifuged at 1600 rpm for 20 minutes under a cooling condition to give complete lymphocytes in the interface.

d) The lymphocytes were collected in a small test tube and washed by centrifuging the lymphocytes twice at 1400 rpm in PBS for 10 minutes under cooling. When erythrocytes were mixed therein, the sample was sterilized by filtration and left with Tris-ammonium chloride at 37° C. for 10 minutes to completely lyse the erythrocytes.

e) After the supernatant was removed, 1 ml PRMI1640 culture solution containing concanavalin A (Con A) at a concentration of 20 μg/ml was introduced into it and well mixed, and the number of the cells were determined by a TATAI hemocytometer. The number of the cells was regulated at $2 \times 10^6$ cells/ml. Thereafter, the lymphocyte suspension was cultured at 37° C. for 48 hours in an 8-well plate for culture.

f) After culture, the supernatant was introduced into a microtube, centrifuged at 6000 rpm for 5 minutes, and the supernatant was transferred to another microtube and stored in a frozen state under cooling at −80° C. until the date of experiment.

2) Measurement of Serum IgE by ELISA

Quantification of IgE antibody present in serum from the subject was carried out in the following ELISA.

a) One hundred μL anti-IgE antibody diluted 100-fold with sodium carbonate buffer was put to a well of a 96-well plate and immobilized on the well at room temperature for 60 minutes.

b) After washing twice with a washing solution, 200 μL post-coat buffer solution was put to each well and incubated at 37° C. for 30 minutes.

c) After washing twice with a washing solution, 100 μL each of subject's serum and IgE standard solutions (1.87, 3.75, 7.5, 15, and 30 ng/ml) were put respectively to wells and incubated at 37° C. for 60 minutes.

d) After washing twice with a washing solution, 100 μL peroxidase (HRP)-labeled antibody diluted 2000-fold was put to each well and incubated at 37° C. for 60 minutes.

e) After washing thrice with a washing solution, 100 μL coloration solution (o-phenylene diamine solution; OPD solution) was put to each well and incubated at room temperature for 30 minutes.

f) After coloration, 100 μL termination solution (3 M sulfuric acid) was put to each well, and the absorbance at 490 nm was measured with an ELISA reader.

g) The concentration of IgE in the subject's serum was calculated according to a standard curve.

The mean concentration of IgE in serum in each group (21 subjects) before and after ingestion of the anti-allergic agent for 3 months, and the difference in mean concentration therebetween, are shown in Table 2.

TABLE 2

| Group | Presence or absence of: | | Ig E level in serum (ng/ml) | | |
|---|---|---|---|---|---|
| | Lotus root | Lactic acid bacterium | before ingestion | after ingestion for 3 months | difference between before and after ingestion for 3 months |
| Example 1 | Extract | present | 79 | 55 | −24 |
| Example 2 | ground product | present | 75 | 53 | −22 |
| Comparative Example 1 | Extract | absent | 73 | 54 | −19 |
| Comparative Example 2 | Extract (2 fold) | absent | 75 | 54 | −21 |
| Comparative Example 3 | absent | present | 71 | 62 | −9 |
| Comparative Example 4 | absent | present (2 fold) | 68 | 63 | −5 |

As is evident from the results in Table 2, the anti-allergic agents of the present invention containing ground lotus and/or a lotus extract and lactic acid bacteria (Examples 1 and 2) were not only recognized to reduce IgE levels in serum as compared with the case where each ingredient was used alone (Comparative Examples 1 and 3), but were also recognized to reduce IgE levels in serum as compared with the case where a double amount of each ingredient was used (Comparative Examples 2 and 4). This result revealed that the anti-allergic agent of the present invention exhibits a synergistic effect on reduction of IgE levels in serum, over the mere additive effect attained by using either the ground lotus and/or lotus extract or lactic acid bacteria alone.

3) Measurement of Serum IgG by SRID Method

Quantification of IgG antibody present in subject's serum was carried out by the following SRID method.

a) Using a micro-syringe washed well with physiological saline, accurately 4 μL each of standard IgG serums (543, 1604, and 3053 mg/dL) and subject's serum were put respectively into wells of an agarose plate for quantification of MBL human IgG (Medical & Biological Laboratories Co., Ltd.). The plate was covered with a plate cover and incubated at room temperature for 24 hours.

b) After the incubation, the diameter of a formed precipitated ring was measured, and the IgG level in the subject's serum was calculated from a standard curve.

The mean concentration of IgG in serum in each group (21 subjects) before and after ingestion of the anti-allergic agent for 3 months, and the difference in mean concentration therebetween, are shown in Table 3.

As is evident from the results in Table 3, the anti-allergic agents of the present invention containing ground lotus and/or a lotus extract and lactic acid bacteria (Examples 1 and 2) were not only recognized to increase IgG levels in serum as compared with the case where each ingredient was used alone (Comparative Examples 1 and 3), but were also recognized to increase IgG levels in serum as compared with the case where a double amount of each ingredient was used (Comparative Examples 2 and 4). This result revealed that the anti-allergic agent of the present invention exhibits a synergistic effect on an increase of IgG level in serum, over the mere additive effect attained by using either the ground lotus and/or the lotus extract or lactic acid bacteria alone.

4) Measurement of IL-2 in a Lymphocyte Culture Supernatant by ELISA

Quantification of IL-2 secreted from lymphocytes in peripheral blood cultured for 48 hours was carried out by the following ELISA.

a) One hundred μL each of subject' serum and IL-2 standard solutions (31, 25, 62.5, 125, 250, 500, and 1000 pg/ml) were put respectively into wells of a 96-well plate for ELISA.

b) Fifty μL biotinated antibody (anti-IL-2) was put into each well and incubated at room temperature for 1 hour.

c) After washing 3 times, 100 mL streptavidin-HRP was put into each well and incubated at room temperature for 30 minutes.

d) After washing 3 times, 100 μL coloring solution (TMB) was put into each well and reacted at room temperature for 10 to 15 minutes in the dark.

TABLE 3

| Group | Presence or absence of: | | Ig G level in serum (ng/dl) | | |
|---|---|---|---|---|---|
| | Lotus root | Lactic acid bacterium | before ingestion | after ingestion for 3 months | difference between before and after ingestion for 3 months |
| Example 1 | Extract | present | 1150 | 1440 | +290 |
| Example 2 | ground product | present | 1230 | 1430 | +200 |
| Comparative Example 1 | Extract | absent | 1250 | 1400 | +150 |
| Comparative Example 2 | Extract (2 fold) | absent | 1120 | 1300 | +180 |
| Comparative Example 3 | absent | present | 1180 | 1280 | +100 |
| Comparative Example 4 | absent | present (2 fold) | 1220 | 1370 | +150 | e) One hundred μL termination solution (sulfuric acid) was put into each well and the absorbance at 450 nm was measured with an ELISA reader.

f) The concentration of IL-2 in the subject's lymphocyte culture supernatant was calculated using a calibration curve.

The mean concentration of IL-2 in lymphocyte culture supernatant in each group (21 subjects) before and after ingestion of the anti-allergic agent for 3 months, and the difference in mean concentration therebetween, are shown in Table 4.

TABLE 4

| | Presence or absence of: | | IL-2 level in serum (pg/ml) | | |
|---|---|---|---|---|---|
| Group | Lotus root | Lactic acid bacterium | before ingestion | after ingestion for 3 months | difference between before and after ingestion for 3 months |
| Example 1 | Extract | present | 21 | 43 | +22 |
| Example 2 | ground product | present | 27 | 41 | +14 |
| Comparative Example 1 | Extract | absent | 22 | 34 | +12 |
| Comparative Example 2 | Extract (2 fold) | absent | 26 | 38 | +12 |
| Comparative Example 3 | absent | present | 24 | 25 | +1 |
| Comparative Example 4 | absent | present (2 fold) | 22 | 24 | +2 |

As is evident from the results in Table 4, the anti-allergic agents of the present invention containing ground lotus and/or a lotus extract and lactic acid bacteria (Examples 1 and 2) were not only recognized to promote production of IL-2 in peripheral blood lymphocytes as compared with the case where each ingredient was used alone (Comparative Examples 1 and 3), but were also recognized to promote production of IL-2 in peripheral blood lymphocytes as compared with the case where a double amount of each ingredient was used (Comparative Examples 2 and 4). This result revealed that the anti-allergic agent of the present invention exhibits a synergistic effect on promotion of production of IL-2 in peripheral blood lymphocytes, over the mere additive effect attained by using either the ground lotus and/or the lotus extract or lactic acid bacteria alone.

5) Measurement of IL-4 in Lymphocyte Culture Supernatant by ELISA

Quantification of IL-4 secreted from lymphocytes in peripheral blood cultured for 48 hours was carried out by the following ELISA.

a) One hundred μL each of subject's serum and IL-4 standard solutions (1.21, 4.4, 8.75, 17.5 and 35 pg/ml) were put respectively into wells of a 96-well plate for ELISA.

b) After washing 3 times, 50 μL biotinated antibody (anti-IL-4) was put into each well and incubated at room temperature for 1 hour.

c) After washing 3 times, 100 μL streptavidin-HRP was put into each well and incubated at room temperature for 30 minutes.

d) After washing 3 times, 100 μL coloring solution (TMB) was put into each well and reacted at room temperature for 15 to 20 minutes in the dark.

e) One hundred μL termination solution (sulfuric acid) was put into each well and the absorbance at 450 nm was measured with an ELISA reader.

f) The concentration of IL-4 in the subject's lymphocyte supernatant was calculated using a calibration curve.

The mean concentration of IL-4 in lymphocyte culture supernatant in each group (21 subjects) before and after ingestion of the anti-allergic agent for 3 months, and the difference in mean concentration therebetween, are shown in Table 5.

TABLE 5

| | Presence or absence of: | | IL-4 level in serum (pg/ml) | | |
|---|---|---|---|---|---|
| Group | Lotus root | Lactic acid bacterium | before ingestion | after ingestion for 3 months | difference between before and after ingestion for 3 months |
| Example 1 | Extract | present | 4.5 | 0.9 | −3.6 |
| Example 2 | ground product | present | 3.9 | 1.2 | −2.7 |
| Comparative Example 1 | Extract | absent | 4.4 | 2.5 | −1.9 |
| Comparative Example 2 | Extract (2 fold) | absent | 4.9 | 2.9 | −2.0 |
| Comparative Example 3 | absent | present | 3.2 | 3.0 | −0.2 |
| Comparative Example 4 | absent | present (2 fold) | 3.9 | 3.5 | −0.4 |

As is evident from the results in Table 5, the anti-allergic agents of the present invention containing ground lotus and/or a lotus extract and lactic acid bacteria (Examples 1 and 2) were not only recognized to inhibit production of IL-4 in peripheral blood lymphocytes as compared with the case where each ingredient was used alone (Comparative Examples 1 and 3), but were also recognized to inhibit production of IL-4 in peripheral blood lymphocytes as compared with the case where a double amount of each ingredient was used (Comparative Examples 2 and 4). This result revealed that the anti-allergic agent of the present invention exhibits a synergistic effect on inhibition of production of IL-4 in lymphocytes in peripheral blood, over the mere additive effect attained by using either the ground lotus and/or the lotus extract or lactic acid bacteria alone.

From the results in Example 3, it is estimated that by oral ingestion of the anti-allergic agent of the present invention, the in vivo production of IL-2 is promoted while the in vivo production of IL-4 is inhibited thereby reducing IgE in serum thereby generating the anti-allergic action.

Examples 4 and 5, Comparative Examples 5 to 9

The influence of the anti-allergic agents of the present invention on mice to which cedar pollen was administered 1) Preparation of the Anti-Allergic Agents Five g of the drug used in Example 1 was milled and then suspended in 100 ml distilled water to give a drug for administration in Example 4.

Five g of the drug used in Example 2 was milled and then suspended in 100 ml distilled water to give a drug for administration in Example 5.

Five g of the drug used in Comparative Example 1 was milled and then suspended in 100 ml distilled water to give a drug for administration in Comparative Example 5.

Ten g of the drug used in Comparative Example 1 was milled and then suspended in 100 ml distilled water to give a drug for administration in Comparative Example 6.

Five g of the drug used in Comparative Example 3 was milled and then suspended in 100 ml distilled water to give a drug for administration in Comparative Example 7.

Ten g of the drug used in Comparative Example 3 was milled and then suspended in 100 ml distilled water to give a drug for administration in Comparative Example 8.

2) Method for Oral Administration of the Drugs and Method for Intranasal Administration of Cedar Pollen Seven days before administration of a cedar pollen extract, 0.5 ml of the drug for administration was orally administered with a sonde to each mouse (BALB/c, female, 3-week-old) (pre-administration). The mouse was given feed (commercially available solid feed) and tap water freely and maintained in a cycle of light and darkness for 12 hours each.

After the pre-administration was carried out for 7 days, the anti-allergic agent (Example 1 or 2 or Comparative Examples 1 to 4) was orally administered to the mouse once per day for 14 days, and simultaneously 25 μL cedar pollen extract (allergen for cedar pollen scratch, manufactured by Torii Pharmaceutical Co., Ltd.) was dropped via a micropipette into the nasal cavity of the mouse, whereby a cedar pollen-sensitized mouse was artificially produced.

In Comparative Example 9, mice to which the same amount of distilled water was administered in place of the drug for administration were used as a control group. In the experiment, 9 mice were used in each group.

3) Method for Collection of Serum

Four hours after final administration in the administration for 14 days, the mice were anesthetized with ether, and from the hepatic artery, blood was collected with a 1-ml syringe and then left at 37° C. for 60 minutes to separate serum.

4) Measurement of Serum IgG by SRID Method (Single Radial Immunodiffusion Method)

IgG levels in serum were measured by the SRID method. The measurement was carried out according to the above-described method.

5) Measurement of Serum IgE by the ELISA Method (Enzyme-Linked Immunosorbent Assay)

IgE levels in serum were measured by the ELISA method. The measurement was carried out according to the above-described method.

6) Culture of Abdominal Macrophages and Determination of Production of TNF-α

Two days before collection of abdominal macrophages, 1 ml thioglycolate was injected into the abdomen. Before blood collection on the day of experiment, 3 to 5 ml cold MEM was injected and the abdomen was well massaged, and macrophages were collected (which was repeatedly carried out 3 to 4 times).

The cells were adjusted to a density of $2 \times 10^6$ cells/ml, then suspended in MEM containing 10 μg LPS (derived from *Escherichia coli*), put into each well of a 12-well plate in a volume of 1 ml/well, and cultured at 37° C. for 24 hours. The culture supernatant was collected and stored at −80° C. until measurement.

TNF-α was measured according to the ELISA method by using a kit manufactured by Wako Pure Chemical Industries, Ltd.

7) Culture of Spleen Cells and Measurement of Production of IL-2 and IL-4

At the time of blood collection, the spleen was aseptically excised. A 200-mesh metal filter for culture was placed in a small Petri dish containing 2 ml RPMI1640 culture solution, and the excised spleen was placed on the filter, and spleen cells were removed from the spleen by using a push surface of a piston of a 5-ml hypodermic syringe.

The obtained spleen cells were suspended finally at a density of $1 \times 10^6$ cells/ml in RPMI1640 containing 10% FBS and 20 μg Con A (concanavalin A). Then, the cell suspension was put into a 12-well plate in a volume of 1 ml/well and cultured for 48 hours in the presence of 5% $CO_2$. The cultured supernatant was stored at −80° C. until measurement.

IL-2 and IL-4 were measured by the ELISA method. The measurement was carried out according to the method described above.

The measurement results are shown in Table 6.

TABLE 6

| Group | Presence or absence of: Lotus root | Presence or absence of: Lactic acid bacterium | Each parameter after administration of the drug for 14 days | | | | |
|---|---|---|---|---|---|---|---|
| | | | IgG (mg/dl) | IgE (ng/dl) | TNF α (pg/ml) | IL-2 (pg/ml) | IL-4 (pg/ml) |
| Example 4 | Extract | present | 958 | 35.3 | 10.1 | 11.9 | 2.1 |
| Example 5 | ground product | present | 987 | 45.3 | 9.8 | 12.4 | 2.0 |
| Comparative Example 5 | Extract | absent | 860 | 70.5 | 20.6 | 11.0 | 3.5 |
| Comparative Example 6 | Extract (2 fold) | absent | 880 | 65.5 | 18.2 | 10.7 | 2.8 |
| Comparative Example 7 | absent | present | 506 | 90.4 | 35.6 | 7.0 | 9.6 |
| Comparative Example 8 | absent | present (2 fold) | 610 | 79.2 | 30.0 | 8.5 | 7.2 |
| Comparative Example 9 | absent | absent | 471 | 92.6 | 39.7 | 6.1 | 10.8 |

As is evident from the results in Table 6, the anti-allergic agents of the present invention containing ground lotus and/or a lotus extract and lactic acid bacteria (Examples 4 and 5) were recognized to exhibit significant inhibition of production of TNF-α by macrophage, when compared not only with the case where each ingredient was used alone (Comparative Examples 5 and 7), but also with the case where a double amount of each ingredient was used (Comparative Examples 6 and 8). This result revealed that the anti-allergic agent of the present invention exhibits a synergistic effect on inhibition of production of TNF-α by macrophage, over the mere additive effect attained by using either the ground lotus and/or the lotus extract or lactic acid bacteria alone.

It was also revealed that the anti-allergic agent of the present invention exhibits a synergistic effect on the ability to reduce IgE levels in serum and on promotion of IL-2 production and inhibition of IL-4 production in spleen cells, over the mere additive effect attained by using either the ground lotus and/or the lotus extract or lactic acid bacteria alone.

INDUSTRIAL APPLICABILITY

The drug, food additive and food of the present invention can be used for anti-allergy, amelioration of pollinosis, reduction in IgE levels in serum, inhibition of IL-4 production and inhibition of TNF production.

The invention claimed is:

1. An agent used for treatment of allergy comprising (1) a mixture of a lotus extract powder prepared by adding water to slices of lotus root, boiling the slices of lotus root and water to produce a boiled product of the slices of lotus root and water, filtrating the boiled product to produce a filtrate, and freeze-dried the filtrate; sporing lactic acid bacteria powder for food; and maltose starch syrup; or (2) a mixture of ground lotus; sporing lactic acid bacteria powder for food; and maltose starch syrup.

2. The agent according to claim 1 which is used as a pollinosis-relieving agent, an agent for lowering IgE levels in serum, an agent for inhibiting the production of IL-4 or an agent for inhibiting the production of TNF.

3. A food used for treatment of allergy comprising (1) a mixture of a lotus extract powder prepared by adding water to slices of lotus root, boiling the slices of lotus root and water to produce a boiled product of the slices of lotus root and water, filtrating the boiled product to produce a filtrate, and freeze-dried the filtrate; sporing lactic acid bacteria powder for food; and maltose starch syrup; or (2) a mixture of ground lotus; sporing lactic acid bacteria powder for food; and maltose starch syrup.

4. The food according to claim 3 which is used as a pollinosis-relieving agent, an agent for lowering IgE levels in serum, an agent for inhibiting the production of IL-4 or an agent for inhibiting the production of TNF.

5. A food additive used for treatment of allergy comprising (1) a mixture of a lotus extract powder prepared by adding water to slices of lotus root, boiling the slices of lotus root and water to produce a boiled product of the slices of lotus root and water, filtrating the boiled product to produce a filtrate, and freeze-dried the filtrate; sporing lactic acid bacteria powder for food; and maltose starch syrup; or (2) a mixture of ground lotus; sporing lactic acid bacteria powder for food; and maltose starch syrup.

6. The food additive according to claim 5 which is used as a pollinosis-relieving agent, an agent for lowering IgE levels in serum, an agent for inhibiting the production of IL-4 or an agent for inhibiting the production of TNF.

* * * * *